United States Patent [19]

Ams et al.

[11] Patent Number: 5,115,126
[45] Date of Patent: May 19, 1992

[54] MEANS FOR CHECKING ENDOSCOPE EQUIPMENT

[75] Inventors: Felix Ams, Kämpfelbach; Roland Schäfer, Bretten-Dürrenbüchig, both of Fed. Rep. of Germany

[73] Assignee: Richard Wolf GmbH, Knittlingen, Fed. Rep. of Germany

[21] Appl. No.: 551,586

[22] Filed: Jul. 11, 1990

[30] Foreign Application Priority Data

Sep. 6, 1989 [DE] Fed. Rep. of Germany ....... 3929562

[51] Int. Cl.⁵ .................... H01J 5/16; G01N 21/00
[52] U.S. Cl. ................... 250/227.11; 250/205; 356/73.1; 340/635
[58] Field of Search ............ 250/227.15, 227.2, 227.11, 250/237 R, 229, 205; 356/73.1; 606/12, 11, 10; 128/634; 340/635

[56] References Cited

U.S. PATENT DOCUMENTS

| 4,543,477 | 9/1985 | Dai et al. ............... 250/227.11 |
| 4,580,557 | 4/1986 | Hertzmann ............... 606/12 |
| 4,632,544 | 12/1986 | Form ................... 356/73.1 |
| 4,633,872 | 1/1987 | Chaffee et al. ........... 606/11 |
| 4,947,033 | 8/1990 | Kordts et al. ........... 250/227.11 |
| 4,994,059 | 2/1991 | Kosa et al. ............. 356/73.1 |

FOREIGN PATENT DOCUMENTS 3515612 11/1985 Fed. Rep. of Germany .
2493559 5/1982 France .................. 606/12

OTHER PUBLICATIONS

"The Dyonics Autobrite Illuminator Manual", Dyonics, Inc. (1984).

Primary Examiner—David C. Nelms
Assistant Examiner—Michael Messinger
Attorney, Agent, or Firm—Panitch Schwarze Jacobs & Nadel

[57] ABSTRACT

A means for checking the iluminating means of an endoscope allows both the lamp of the endoscope and the light-guide cable to be checked for their operating conditions. For this purpose, the checking means has a beam splitter positioned in the beam path from the lamp which conveys part of the quantity of light emitted by the lamp to a detecting means. A detecting means provided with a device to receive the distal end of the light-guide cable picks up the quantity of light coming from the cable. From the signal derived therefrom and the signal generated by the detecting means, the transmission factor is found in a calculating circuit by quotient formation and is shown on a display. In this way it is possible to determine whether the transmission factor of the light-guide cable will allow the objects which are going to be viewed to be adequately illuminated or whether the cable needs to be replaced.

3 Claims, 1 Drawing Sheet

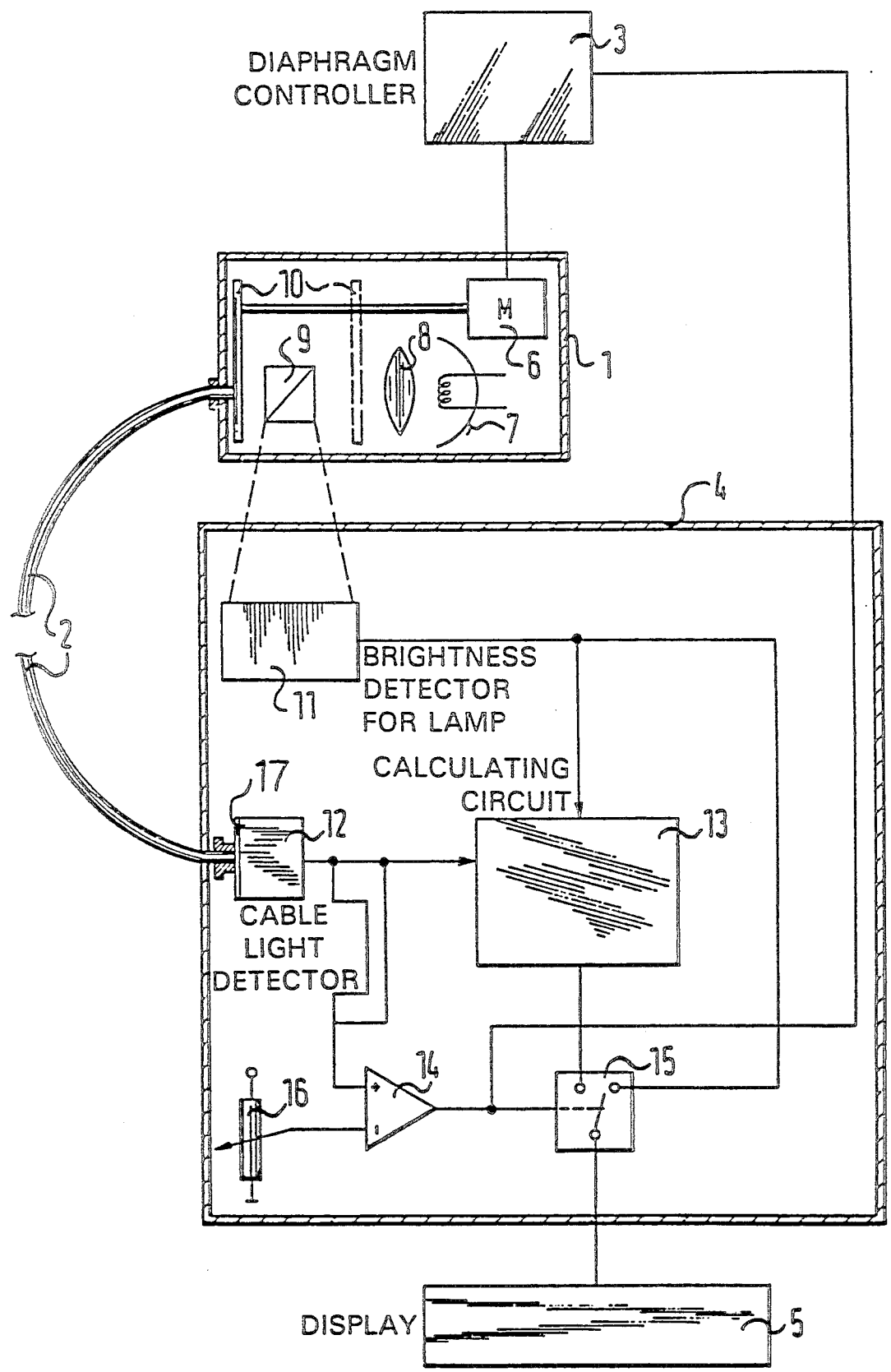

MEANS FOR CHECKING ENDOSCOPE EQUIPMENT

BACKGROUND OF THE INVENTION a) Field of the Invention

The invention relates to a means for checking the lamp of a light source unit producing the illuminating light for an endoscope and a light-guide cable which conveys the illuminating light to the object being observed b) Description of the Prior Art To examine cavities which are difficult of access, such as body cavities, use is made of endoscopes. Since the objects which are of interest in the cavities are often photographed or shown in monitors by means of television cameras, the endoscopes employed use controllable illumination facilities which are intended to ensure that the objects being observed are ideally illuminated. In this case the light produced by the light sources is transmitted to the endoscope along light-guide cables.

The operation of the light-guide cable of endoscopic apparatus may be adversely affected by the fracture of individual fibers. e.g. due to severe bending stresses, by ageing or by similar causes, and this may mean that the objects to be viewed with the endoscope can no longer be properly illuminated. Particularly with arc lamps, there is also a reduction in the quantity of light which can be emitted as the time in use lengthens, so that illumination is degraded for this reason too. Hence it is useful in endoscopic applications, and particularly in medicine, for it to be possible for the correct operation of the means of illumination to be checked. What is achieved by making a check of this kind is that faulty operation of the means of illumination or the light-guide cable is detected before the endoscope is introduced into the body cavity and in this way any unnecessary stress on the patient caused by the replacement of a faulty light-guide cable or a lamp which is no longer producing enough light can be avoided.

A method of checking a light source for endoscopes is known from DE-OS 3515612. In the embodiment disclosed therein what are checked are the light emitted from the lamp when operating continuously and as a flash-lamp, the operation of the shutter vane, the operation of the diaphragm and the data transmission between control unit and camera. What is not checked is the operation of the light-guide cable.

Another means of checking the supply of light can be seen in the operating instructions for a light source with a diaphragm controlling arrangement which is made by the Dyonics Company. It includes an arrangement for checking the light-guide cable. To check the lamp, its brightness is sensed by a photo-resistor and is shown in the form of a bar plot. To check the light-guide cable, it is inserted in the socket of a brightness measuring device, which causes the controller of the motor driving the diaphragm to open the latter completely. The brightness level so measured is also shown as a bar plot, and the height of the bar provides information on the condition of the lamp and light guide cable.

One disadvantage from which this means suffers is that the system has to be calibrated to suit the diameter of the bundle of fibers making up the light-guide cable which is used and if a fiber bundle of a different diameter is used, there are inaccuracies in the measurements. Also, the brightness levels measured are merely indicated and the user has to interpret these levels for himself, i.e. has to estimate the transmission for himself, and because of this misinterpretations cannot be ruled out.

Hence the main object of the present invention is to provide a means of measurement for light sources for endoscopes with which the lamp and the light-guide cable can be checked for satisfactory operation by automatic analysis.

SUMMARY OF THE INVENTION

To this end, the present invention consists in a means for checking the lamp of a light source unit producing the illuminating light for an endoscope and for checking a light-guide cable which conveys the illuminating light to the object being observed, characterised by a transmission measuring means able to be integrated into the light source unit, comprising a means for detecting the quantity of light emitted by the lamp into the light-guide cable, a means for detecting the quantity of light emerging from the distal end of the light-guide cable, and a calculating circuit to determine the transmission factor in the form of the quotient of the quantities of light detected.

By means of the invention there is provided the advantage that when the endoscope equipment and the means of illumination are being checked, the operation of the light-guide cable, also, can easily be checked irrespective of the diameter of the latter's fiber bundle, that is to say without the need to use special external measuring devices because, with the design according to the invention, the transmission measuring means are integrated into the unit for generating the light and controlling its quantity.

To check the quantity of light emitted by the lamp, the light source unit preferably has a beam splitter positioned in the beam path from the lamp to divert off part of the quantity of light emitted.

In a means in which the light source unit, which includes a controllable diaphragm, is provided with a control means for controlling the quantity of light fed into the light-guide cable, a logic link with the transmission measuring means can be achieved by connecting, downstream of the means for detecting the quantity of light emerging from the distal end of the light-guide cable, a comparator which compares the signal generated by the detecting means with a brightness threshold level settable by an adjuster and which feeds a signal to the diaphragm controlling means if this level is exceeded, as a result of which the diaphragm is set to a predetermined position.

To allow a visual check on the various results of the measurements, the transmission measuring means preferably has a changeover switch which feeds to the display the signal for the brightness of the lamp which is generated by the detecting means if the brightness threshold value is not reached and a signal representing the transmission factor e.g. in the form of a numerical value, which is calculated by the calculating circuit if the brightness threshold value is exceeded.

BRIEF DESCRIPTION OF THE DRAWING

In order that the invention may be more readily understood, an embodiment thereof will now be described, by way of example, with reference to the accompanying drawing which is a block diagram of a means for checking the lamp of a light source unit producing the illuminating light for an endoscope and for checking a light guide cable which conveys the illuminating light to the object being observed.

DESCRIPTION OF THE PREFERRED EMBODIMENT

In essence, the means formed in accordance with the invention comprises a light source unit 1, which feeds focussed, filtered light to the inlet face of a light-guide cable 2, a diaphragm controlling means 3 which transmits the control signals required for controlling the quantity of light to the light source unit 1, a transmission measuring means 4 for measuring the transmission factor, and a display 5 to show the transmission factor and the brightness of the lamp.

Arranged in the light source unit 1 are a motor 6, a lamp 7, an arrangement 8 for focussing and filtering the light radiated by the lamp 7, a beam splitter 9 which feeds part of the light from the lamp 7 to a means 11 for detecting the brightness of the lamp 7, and a diaphragm 10 for controlling the quantity of light. Arranging the beam splitter 9 in the path of the light has the advantage that it rules out the sort of measurement errors which would be caused for example by using scattered light to measure the brightness of the lamp. By means of the motor 6, the diaphragm 10 is opened or closed, to the degree indicated by the signals fed to the motor for the diaphragm controlling means 3, to control the input of light into the light-guide cable 2.

The transmission measuring means 4 comprises a means 12 for detecting the quantity of light emerging from the distal end of the light-guide cable 2. The detecting means 12 is connected to a calculating circuit 13 and to a comparator 14 which compares the threshold brightness level set by means of an adjuster 16 with the level measured in the detecting means 12.

If the signal conveyed to the comparator 14 exceeds this threshold brightness level, a changeover switch 15 feeds the signal calculated by the calculating circuit 13, which represents the transmission factor, to the display 5 where it is shown in visible form. At the same time the signal from the comparator is fed to the diaphragm controlling means 3, which in turn feeds a control signal to the motor 6 of the light source unit 1, in response to which the diaphragm 10 is set to a predefined position (calibration position), such as the fully open position.

The transmission factor mentioned is the ratio between the signal from the means 12 for detecting the quantity of light emerging from the light-guide cable 2 and the signal from the means 11 for detecting the quantity of light emitted by the lamp 7.

If the brightness threshold value is not reached or if the light-guide cable 2 is not connected to the detecting means 12 of the transmission measuring means 4 to allow transmission to be measured, the display 5 shows the brightness of the lamp 5, e.g. as a numerical value. This is done by causing the brightness level measured by the detecting means 11 from the quantity of light directed onto it by the beam splitter 9 of the light source unit 1 to be transmitted to the display 5.

If the light-guide cable 2 is connected to the detecting means 12 to allow transmission to be checked and if the lamp 7 of the light source unit 1 is on, the detecting means 12 generates a signal and directs it both to the calculating circuit 13 and to the comparator 14. In the comparator 14, the value transmitted by the detecting means 12 is compared with the brightness level set by the adjuster 16. If the latter level is exceeded, the output signal from the comparator changes over the changeover switch 15, and as a result the transmission factor for the light-guide cable 2 calculated in the calculating circuit 13 is shown on the display 5. The light-guide transmission factor is found in the calculating circuit 13 by forming the quotient of the output signals from the light detecting means 11 and 12 which are fed to it. This ensures that the nature and condition of the lamp 7 do not play any part in the assessment of the ability of the light-guide cable 2 to operate properly. In this way it is possible to ascertain whether the transmission factor of the light-guide cable 2 allows adequate illumination of the objects being viewed or whether the cable 2 needs to be replaced.

To ensure that the process of determining the transmission factor is not dependant on the diameter of the bundle of fibers forming the given light-guide cable, a diaphragm 17 is so mounted in the device for receiving the light-guide cable in the detecting means 12 that, irrespective of the actual cross-section of the fiber bundle, it is always the same portion of the cross-section of the fiber bundle which is used to sense the quantity of light passing through the light-guide cable.

Both the means 11 for detecting the quantity of light emitted by the lamp 7 and the means 12 for detecting the quantity of light emitted from the light-guide cable 2 are photo-receivers, e.g. photodiodes, which generate an electrical signal corresponding to the quantity of light received. The quantity of light emitted by the lamp 7 may be determined in other ways, such as from the voltage to the lamp in the case of arc lamps supplied by a power source.

To allow light sources whose diaphragms close hermetically to be used, the device for connecting the light-guide cable to the detecting means 12 may be so designed that when the light-guide cable 2 is connected up, the diaphragm 10 of the light source unit 1 is opened slightly so that a quantity of light sufficient to exceed the threshold brightness level is fed to the detecting means 12, thus causing the motor 6 of the light source unit 1 to set the diaphragm 10 to the position selected as the calibration setting.

It is equally possible for the diaphragm to be positioned between the beam splitter 9 and the lamp 7, thus enabling the calculated transmission factor to be found correctly in the same way, irrespective of the position of diaphragm 10.

When the light-guide cable 2 is disconnected from the detecting means 12, an appropriate signal from the diaphragm control means 3 causes the diaphragm to be completely closed by the motor 6, thus obviating the possibility of the user being dazzled.

It should be appreciated that the invention is not limited to the embodiment herein described but includes all modifications and variations falling within the scope of the invention.

We claim:

1. Apparatus for checking a lamp of a light source unit producing illuminating light for an endoscope and for checking a light-guide cable which conveys the illuminating light to an object being observed, said light source unit having a controllable first diaphragm through which light is conducted to the light-guide cable and means for controlling the quantity of light fed into the light-guide cable, comprising beam splitting means positionable in a beam path of the lamp for diverting a first quantity of the illuminating light, first means for detecting said first quantity of illuminating light to check said lamp, second means for detecting a second quantity of light emerging from a distal end of the light-guide cable, comparator means for comparing a first signal generated by said second detecting means with a brightness threshold level settable by an adjuster, whereby said comparator feeds a second signal to said control means if the level is exceeded whereby said control means sets said first diaphragm in a predetermined position in response to said second signal, and calculating circuit means for determining a quotient of said second an first quantities of detected light, said quotient representing a transmission factor to check said light guide cable.

2. Apparatus according to claim 1 wherein said second detecting means includes second diaphragm means for receiving the distal end of the light-guide cable.

3. Apparatus according to claim 1 further comprising a changeover switch responsive to said comparator, whereby said changeover switch fees to a display a third signal representing brightness of the lamp which is generated by said first detecting means if the brightness threshold level is not reached, and said changeover switch feeds to a display a fourth signal representing the transmission factor f the light-guide cable if the threshold brightness level is exceeded.

* * * * *